United States Patent [19]

Yau

[11] Patent Number: 4,693,854

[45] Date of Patent: Sep. 15, 1987

[54] GENERATOR FOR HAIR STYLING MOUSSE

[75] Inventor: Yuk M. Yau, Shatin, Hong Kong

[73] Assignee: Conair Corporation, Edison, N.J.

[21] Appl. No.: 915,695

[22] Filed: Oct. 6, 1986

[51] Int. Cl.⁴ .............................................. B01F 3/04
[52] U.S. Cl. .............................. 261/84; 261/DIG. 26;
521/917
[58] Field of Search ........................ 261/DIG. 26, 84;
521/917

[56] References Cited

U.S. PATENT DOCUMENTS

| | | | |
|---|---|---|---|
| 2,146,605 | 2/1939 | Timpson | 261/DIG. 26 |
| 2,969,960 | 1/1961 | Gurley, Jr. | 521/917 |
| 2,988,343 | 6/1961 | Edwards et al. | 261/84 |
| 3,341,468 | 9/1967 | Rosen | 261/84 |
| 3,389,836 | 6/1968 | Wakeman | 261/DIG. 26 |
| 3,430,865 | 3/1969 | McDougall | 261/DIG. 26 |
| 4,027,993 | 6/1977 | Wolff | 261/DIG. 26 |
| 4,132,838 | 1/1979 | Kreuer et al. | 521/917 |
| 4,299,925 | 11/1981 | Ogden | 521/917 |

Primary Examiner—Tim Miles
Attorney, Agent, or Firm—Haynes N. Johnson

[57] ABSTRACT

A styling mousse generator adapted to foam a liquid and deliver foamed styling mousse for use in hair treatment and the like having a liquid reservoir in its lower portion, means for filling the reservoir, a fan and motor above the reservoir, a fan inlet and a fan outlet, a foam delivery tube leading from the reservoir to the fan inlet, a liquid inlet duct (coming from the reservoir) and an air inlet duct (coming from a location higher than the reservoir liquid level) at an acute angle to each other (to create a Bernoulli type effect) and leading to the foam delivery tube, and a passageway leading from the fan outlet to a foam outlet. The passageway may be serpentine or include frictional, agitating means to warm the foam.

10 Claims, 9 Drawing Figures

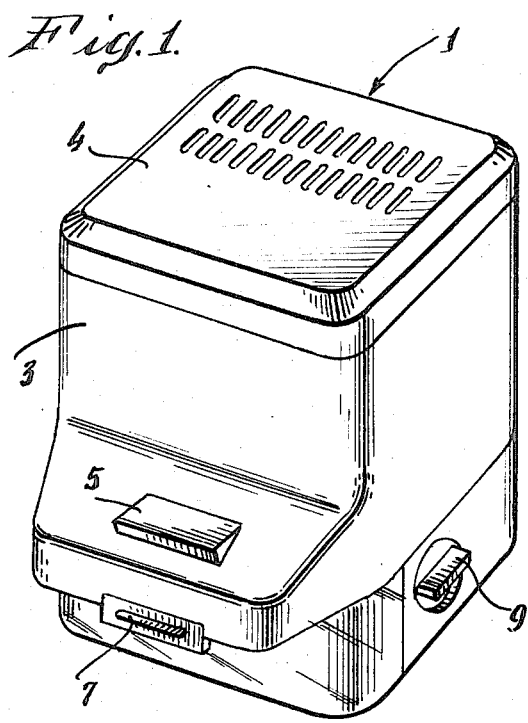
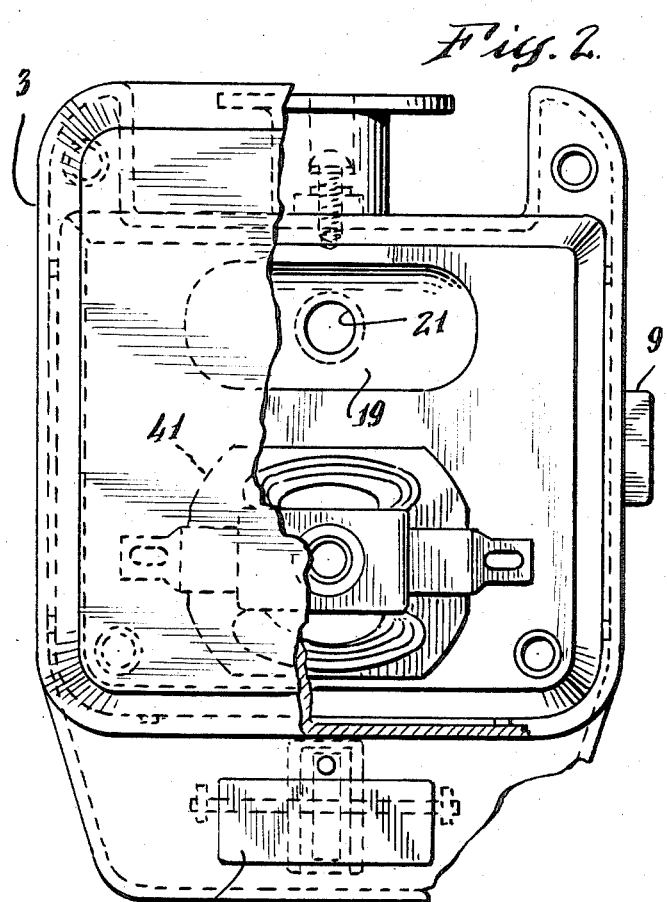
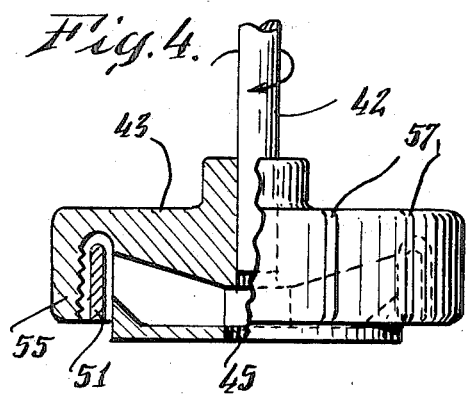
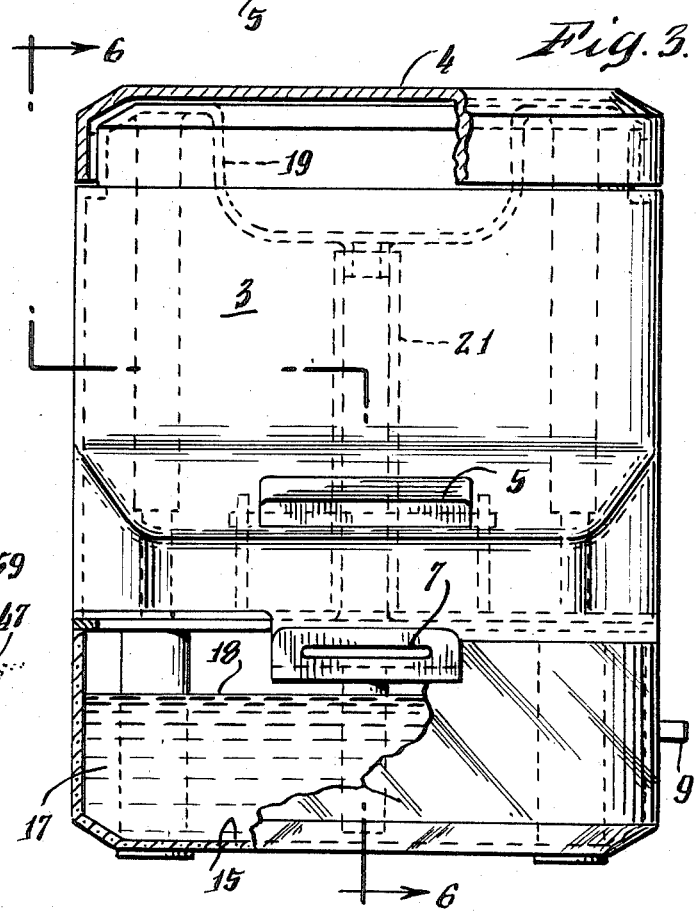
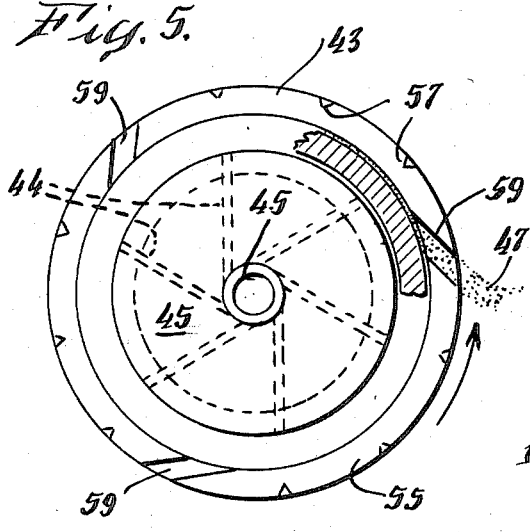

4,693,854

GENERATOR FOR HAIR STYLING MOUSSE

FIELD OF THE INVENTION

This invention relates to the field of mousse generators, used for preparing styling mousse for application to the hair. The mousse is prepared from a liquid, i.e., lotion, hair-set, or the like, used in hair treatment. The generator takes the liquid and aerates it to the form of a foamed mousse and heats it.

This invention improves and simplifies the structure of such generators, locating the liquid storage in the lower portion of the unit; this prevents harmful leakage and also protects the motor and fan system from the liquid.

BRIEF SUMMARY OF THE INVENTION

A mousse machine or generator is provided with a liquid reservoir in its base. A vertical foam delivery tube projects into the reservoir. Liquid and air are drawn upwardly through the tube by the suction created by the central inlet of a centrifugal fan positioned above the reservoir. The tube has an air inlet and a liquid inlet which together form a Bernoulli-type suction device; this causes the liquid to be aerated and foamed as it is drawn upwardly.

The foamed combination is drawn from the foam delivery tube into the fan inlet and dispersed radially. It is heated frictionally by following a serpentine path and by the relative motion of a series of serrations, grooves, or ribs on the surfaces of concentric shrouds located in the outlet path for the mousse.

DESCRIPTION OF THE DRAWINGS

FIG. 1 is a perspective view of the mousse machine of my invention.

FIG. 2 is a top plan view partially broken away to show internal structure.

FIG. 3 is a front elevation partially broken away to show internal structure.

FIG. 4 is a perspective view, partially in section, of the centrifugal fan.

FIG. 5 is a bottom plan view, partially broken away, of the fan structure.

DETAILED DESCRIPTION OF THE INVENTION

Figure 6:
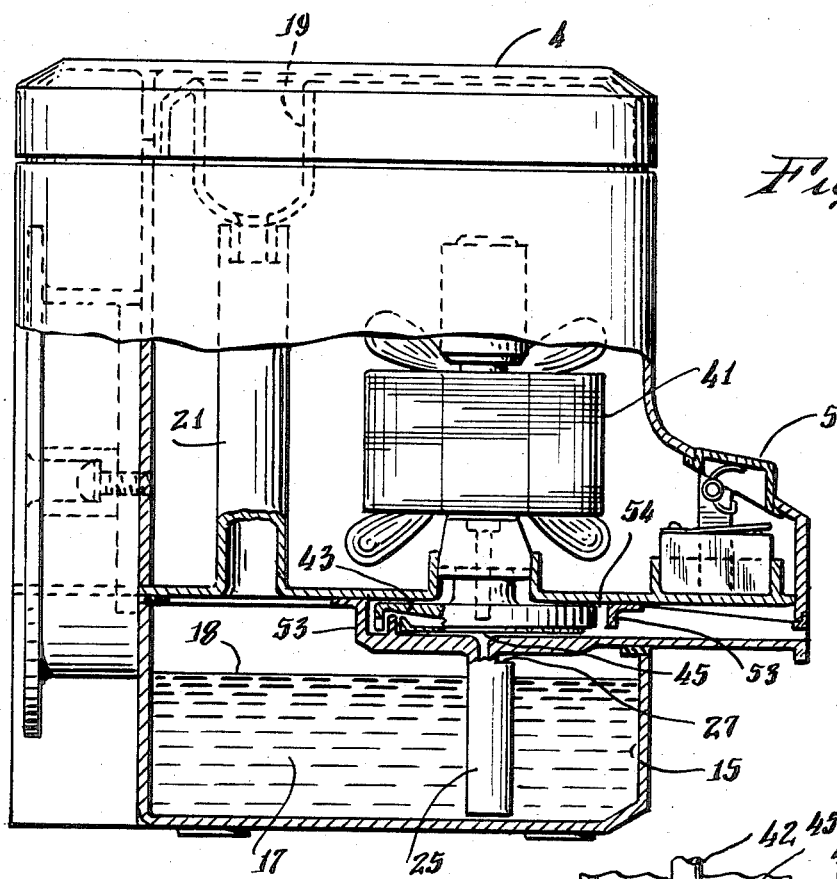
FIG. 6 is a vertical section, taken on line 6—6 of FIG. 3.

The mousse machine or generator 1 is shown in perspective in FIG. 1. That view shows the housing 3 with its removable top 4, an actuating switch button 5, an outlet 7 for the foamed mousse, and a drain plug 9 for the reservoir which holds the liquid prior to foaming.

The remaining figures give more details of the structure.

A reservoir 15 for liquid 17 to be foamed is located within and at the bottom of the housing 3. The reservoir is filled from the top of the unit by removing top 4 and pouring the liquid 17 into the filler basin 19, from which it flows through filler tube 21 to reservoir 15. The level of liquid in the reservoir is indicated in the drawings by the numeral 18.

A centrifugal fan 43, driven by motor 41 (controlled by switch 5), is positioned within the housing 3 and above the reservoir 15. Fan 43 has vanes 44 and a central fan inlet 45. A foam delivery tube 25 runs vertically from fan inlet 45 to a point slightly above the bottom of reservoir 15. Thus, suction created in the fan inlet when the fan is operating creates a suction in the foam delivery tube 25 which can be used to draw liquid 17 and air into the fan inlet 45.

The lower portion of delivery tube 25 has a central liquid duct 31 leading from the liquid 17 in the reservoir 15 to the delivery tube 25, so that liquid 17 can enter the tube 25 through duct 31 and pass upwardly to the fan inlet 45.

An air inlet tube 27 is attached to delivery tube 25 and has its air inlet portion at the top, above the maximum level 18 of the liquid 17 in the reservoir 15. The lower end of air inlet tube 27 leads to one or more small, upwardly directed air inlet ducts 29 leading to the lower portion of tube 25 near where liquid inlet duct 31 enters tube 25. Thus, the air inlet ducts 29 and the liquid inlet duct 21 are at an acute angle to one another as they enter tube 25. The cross-sectional area of air inlet tube 27 (and so that of the air inlet ducts 29) is greater than that of liquid duct 31.

Figure 7:
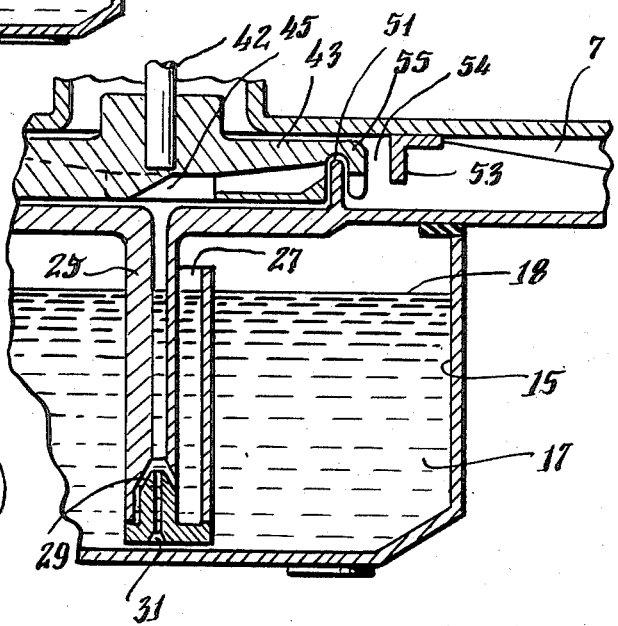
FIG. 7 is a partial vertical section through the reservoir and fan portion and showing the mousse outlet. In this view the mousse machine is not operating.
Figure 8:
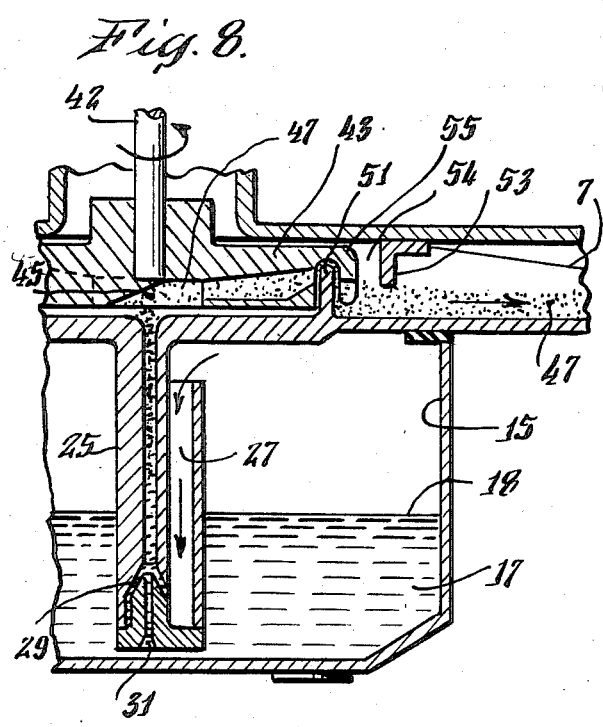
FIG. 8 is similar to FIG. 7 except that the machine is operating and delivering mousse.
Figure 9:
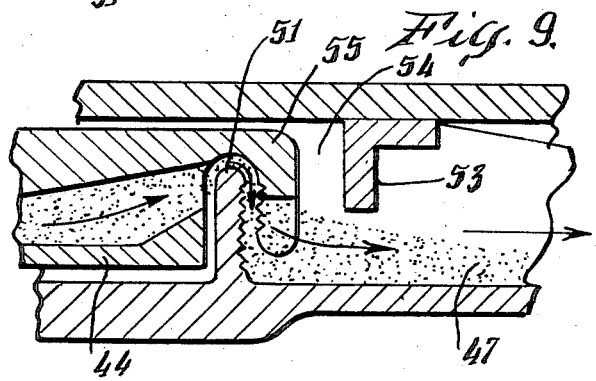
FIG. 9 is a detail from FIG. 8 showing the gate between the centrifugal fan and the mousse outlet.

FIG. 7 shows the relation of the liquid to the ducts 29 and 31 and delivery tube 25 when fan 43 is not operating. As would be expected, the ducts and delivery tube fill with liquid 17 until the liquid level within tube 25 is the same as the liquid level 18 in reservoir 15.

By contrast, when fan 43 is operating, the suction created will draw air and liquid upwardly through tube 25 and so lower the liquid level within tube 25. When the fan is first started, it will draw the liquid primarily from that within air inlet tube 27 (because of the larger cross-section). Thereafter, it will draw air through air inlet ducts 29, which air, by an action resembling the Bernoulli effect, will serve to draw the liquid 17 in through the liquid inlet duct 31. This action creates a foamed mousse 47 which fills delivery tube 25 and passes upwardly through tube 25 to enter fan inlet 45.

Motor 41 has a vertical rotor 42 and, so, the vanes 44 of fan 43 rotate about a vertical axis, tending to throw the foamed mousse 47 horizontally. Vanes 44 rotate within a circular fan housing 53, the fan housing defining a fan plenum chamber 54. Mousse outlet 7 leads from this housing 53. Plenum chamber 54 has a fixed concentric shroud 51 within it. Between housing 53 and shroud 51 is a rotating shroud 55 integral with the vane structure 44. Shroud 55 has mousse exit slots 59 along its bottom edge. It also has a series of serrations or vertical ribs 57 on its outer surface to generate frictional heat.

After the foamed mousse 47 has been drawn up within tube 25 by the suction created by fan 43, it enters fan inlet 45. It is then forced outwardly by centrifugal force towards fixed shroud 51. The foamed portion then passes over shroud 51, usually leaving any unfoamed liquid 17 behind (to later drain back to the reservoir). The foamed mousse is then driven through the exit slots 59 in the rotating shroud 55 and thence out through foam outlet 7. The shrouds and plenum define a passageway from the fan vanes to the mousse outlet 7 in which the styling mousse travels.

In the course of this serpentine travel through these interrelated shrouds the foamed styling mousse 47 is subjected to sufficient agitation and frictional forces to cause it to be warmed. Consequently, the product of this mousse generator is a warm, foamed styling mousse, made from the liquid first placed in reservoir 15.

I claim:

1. A styling mousse generator adapted to foam a liquid and deliver foamed mousse for use in hair treatment and the like, said mousse generator including a housing including a liquid reservoir in the lower portion thereof, means for filling said reservoir, a foam outlet leading from said housing, a fan and motor positioned within said housing and above said reservoir, said fan having a fan inlet and a fan outlet, and a foam delivery tube leading from the lower portion of said reservoir to said fan inlet, said foam delivery tube including a liquid inlet duct proximate to the lower end thereof for receiving liquid from said reservoir, an air inlet tube associated with said foam delivery tube and having its air inlet end above the expected liquid levels of said reservoir, at least one air inlet duct leading from said air inlet tube into said foam delivery tube proximate to said liquid inlet duct, and a passageway leading from said fan outlet to said foam outlet, whereby actuation of said fan will cause air and liquid to be intermixed in said foam delivery tube, to be drawn through said fan, and to be discharged through said foam outlet.

2. A styling mousse generator as set forth in claim 1 in which said fan is a centrifugal fan and is in a fan housing which defines a fan plenum chamber forming said passageway.

3. A styling mousse generator as set forth in claim 2 in which said plenum chamber includes at least one rotating shroud therein with a frictional surface for generating heat to warm said mousse.

4. A styling mousse generator as set forth in claim 1 in which said passageway is serpentine.

5. A styling mousse generator as set forth in claim 1 in which said fan is in a fan housing which defines a fan plenum chamber, a plurality of concentric shrouds are positioned within said plenum chamber, and said shrouds define a serpentine passageway for foam leaving said fan.

6. A styling mousse generator as set forth in claim 1 in which the total cross-sectional area of said air inlet ducts is greater than that of said liquid inlet duct.

7. A styling mousse generator as set forth in claim 1 in which said air inlet ducts and said liquid inlet ducts are so positioned relative to one another as to create a Bernoulli effect and thereby cause liquid to be foamed as it is drawn into said foam delivery tube.

8. A styling mousse generator as set forth in claim 1 including a filler basin within said housing and higher than said reservoir and a filler tube leading from said filler basin to said reservoir, whereby said reservoir may be filled with liquid by pouring same into said filler basin.

9. In a mousse generator adapted to foam liquid into a mousse, said mousse generator including a housing having a liquid reservoir therein and a driven centrifugal fan with an inlet opening therein, said reservoir being positioned below said fan, that improvement including a substantially vertical foam delivery tube leading from a position proximate to the bottom of said reservoir to said inlet opening, at least one air inlet duct and at least one liquid inlet duct leading to said foam delivery tube near the lower end thereof, and an air inlet tube leading from a position higher than the liquid level in said reservoir to said air inlet duct, and said air inlet duct and said liquid inlet duct being positioned at an acute angle relative to one another at their point of entry into said foam delivery tube so as to create a foaming action between entering air and liquid when said fan is operated, whereby said liquid is foamed as it enters said foam delivery tube.

10. In a mousse generator as set forth in claim 9, that inmprovement in which said acute angle is such as to create a Bernoulli-like effect.

* * * * *